United States Patent
Danzer

(10) Patent No.: US 8,385,508 B2
(45) Date of Patent: Feb. 26, 2013

(54) SCATTERED RADIATION COLLIMATOR ELEMENT, SCATTERED RADIATION COLLIMATOR, RADIATION DETECTOR UNIT AND METHOD FOR PRODUCING A SCATTERED RADIATION ABSORBER ELEMENT

(75) Inventor: Ludwig Danzer, Wendelstein (DE)

(73) Assignee: Siemens Aktiengesellschaft, Munich (DE)

( * ) Notice: Subject to any disclaimer, the term of this patent is extended or adjusted under 35 U.S.C. 154(b) by 57 days.

(21) Appl. No.: 12/382,104

(22) Filed: Mar. 9, 2009

(65) Prior Publication Data

US 2009/0225953 A1 Sep. 10, 2009

(30) Foreign Application Priority Data

Mar. 10, 2008 (DE) .................. 10 2008 013 414

(51) Int. Cl.
*G21K 1/02* (2006.01)
*G21K 1/00* (2006.01)
(52) U.S. Cl. ........................... 378/147; 378/154
(58) Field of Classification Search ........... 378/147–155
See application file for complete search history.

(56) References Cited

U.S. PATENT DOCUMENTS

| | | | | |
|---|---|---|---|---|
| 4,096,391 A | * | 6/1978 | Barnes | 378/146 |
| 5,231,655 A | * | 7/1993 | Wei et al. | 378/147 |
| 6,072,188 A | * | 6/2000 | Arakawa | 250/582 |
| 6,075,840 A | * | 6/2000 | Pellegrino et al. | 378/154 |
| 6,912,266 B2 | | 6/2005 | Spahn | |
| 2001/0002699 A1 | | 6/2001 | Such et al. | |
| 2006/0055087 A1 | | 3/2006 | Freund et al. | |
| 2007/0064878 A1 | | 3/2007 | Heismann | |

FOREIGN PATENT DOCUMENTS

| | | |
|---|---|---|
| DE | 10026160 A1 | 11/2001 |
| DE | 202 20 461 | 8/2003 |
| DE | 102004027158 A1 | 12/2005 |
| DE | 102005044650 A1 | 3/2007 |

OTHER PUBLICATIONS

German Office Action for German Patent Application No. 10 2008 013 414.7 dated Jul. 25, 2012.

* cited by examiner

*Primary Examiner* — Irakli Kiknadze
(74) *Attorney, Agent, or Firm* — Harness, Dickey & Pierce, P.L.C.

(57) ABSTRACT

A scattered radiation collimator element is disclosed for producing a scattered radiation collimator for absorbing scattered radiation which is generated during an examination of an object by interaction of x-ray or gamma radiation used for this purpose. For the purposes of simplification and reducing costs during production, in at least one embodiment, the scattered radiation collimator element includes a plurality of absorber elements, designed in a strip-like or filament-like fashion and arranged adjacent to one another to form an absorber surface.

22 Claims, 2 Drawing Sheets

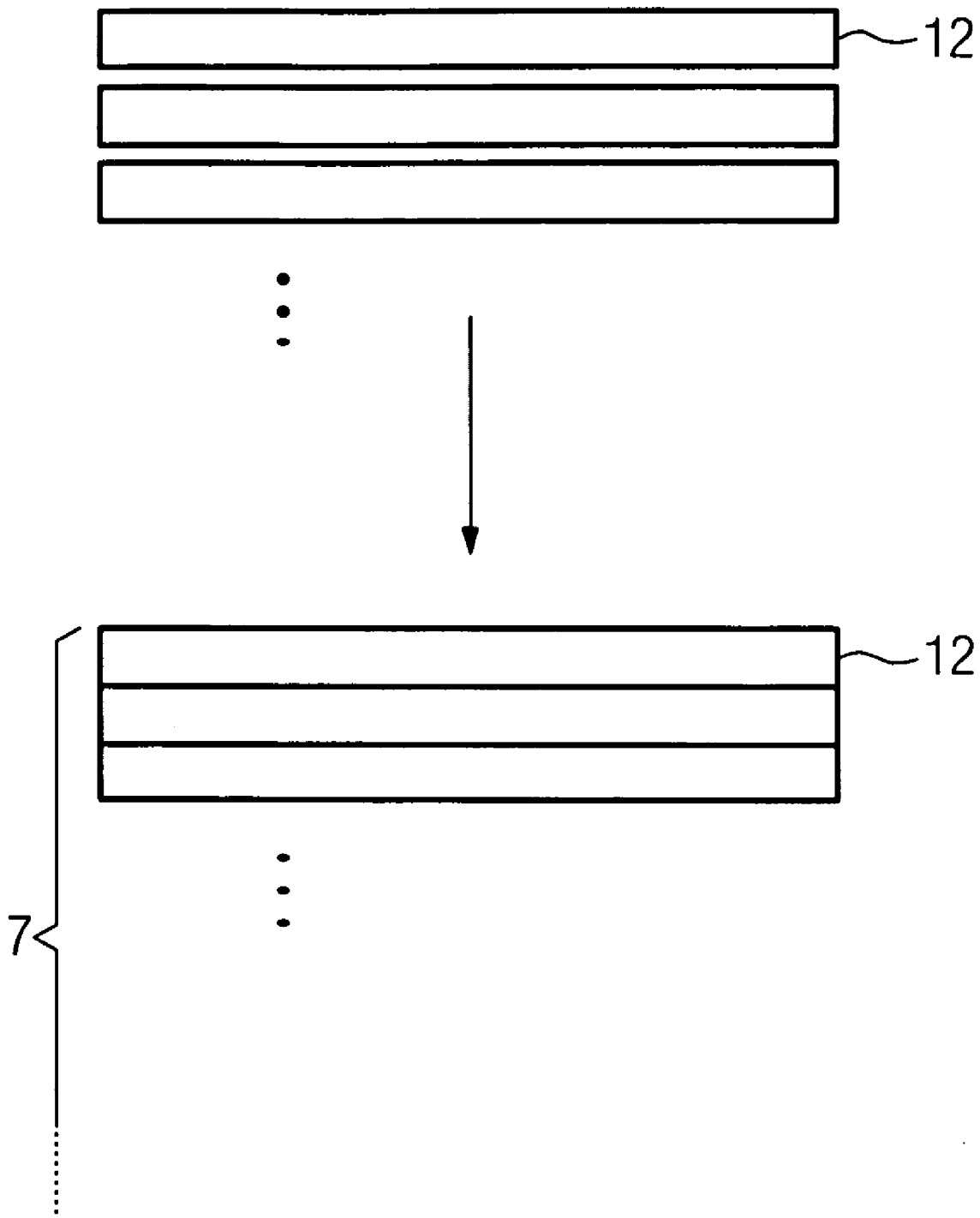

SCATTERED RADIATION COLLIMATOR ELEMENT, SCATTERED RADIATION COLLIMATOR, RADIATION DETECTOR UNIT AND METHOD FOR PRODUCING A SCATTERED RADIATION ABSORBER ELEMENT

PRIORITY STATEMENT

The present application hereby claims priority under 35 U.S.C. §119 on German patent application number DE 10 2008 013 414.7 filed Mar. 10, 2008, the entire contents of which is hereby incorporated herein by reference.

FIELD

At least one embodiment of the invention generally relates to a scattered radiation collimator element, a scattered radiation collimator, a radiation detector unit and/or a method for producing a scattered radiation absorber element.

It is well known that when x-ray or gamma radiation (also referred to as radiation in the following text for the sake of brevity) is transmitted through an object to be examined by the radiation, scattered radiation is generated as a result of the interaction of this radiation with the object. This scattered radiation is undesirable in examinations such as x-ray computed tomography because it leads to artifacts in images reconstructed from the recorded attenuation values.

In order to suppress this undesirable scattered radiation, so-called scattered radiation collimators are used in and, in the direction of incidence of the radiation, inserted upstream of the radiation detectors of transmission tomography equipment such as x-ray computed tomography scanners. In the case of x-ray computed tomography scanners with one x-ray source and one radiation detector for detecting the x-ray radiation generated by the x-ray source, such a scattered radiation collimator in general consists of a multiplicity of scattered radiation collimator elements, preferably aligned toward the focus of the x-ray source; i.e. they are preferably confocal collimator elements. The scattered radiation collimator elements can be produced using a material which absorbs sufficient amounts of scattered radiation such as lead, tungsten or the like, and are also known as collimator sheets in this context.

Due to the fact that the collimator sheets are arranged upstream of the radiation detector and have an absorption cross-section in the direction of incidence of the radiation which is not equal to zero, the sheets also absorb part of the radiation that has not been scattered. That is to say, the radiation detector lies in the shadow of the collimator sheets. In order to at least reduce the shadow, particularly in detection sensitive regions, and the artifacts connected to this, the collimator sheets should have a particularly even thickness and high planarity. The thickness of the collimator sheets in x-ray computed tomographic, medical imaging is of the order of 100 micrometers.

The challenge in producing such delicate collimator sheets lies in ensuring a thickness tolerance which is as small as possible whilst at the same time ensuring a high planarity. Some applications, such as x-ray computed tomography, furthermore require a high mechanical stability on account of the acceleration forces occurring when an object to be examined is scanned in a circular or helical fashion. High thickness tolerances and low planarity increase the probability of shadow-dependent artifacts. This challenge becomes even more important when the scattered radiation collimator elements become larger. The posed requirements for the scattered radiation collimator elements result in high production complexity and, in conjunction with this, relatively high production costs.

SUMMARY

In at least one embodiment of the invention, at least one of the disadvantages in accordance with the prior art is removed or at least lessened. In particular, a scattered radiation collimator element of at least one embodiment is intended to be provided which can be produced in a simple and cost-effective manner, and, in particular, has a relatively large absorber surface. It is a further goal to provide a scattered radiation collimator element which can be produced in a simple and cost-effective manner and which rises to the challenge of high mechanical stability, in particular in x-ray computed tomography. Furthermore, a scattered radiation collimator and a radiation detector unit are intended to be provided which implicitly achieve the object posed with regard to the scattered radiation collimator element. Moreover, it is a goal to provide a method which makes it possible to produce the scattered radiation collimator element in a simple and cost-effective manner and which, in particular, has a high mechanical stability.

A first aspect of at least one embodiment of the invention relates to a scattered radiation collimator element for producing a scattered radiation collimator for absorbing scattered radiation which is generated during an examination or scanning of an object by interaction of x-ray or gamma radiation used for this purpose with the object.

During the examination or scanning of the object, for example by means of an x-ray computed tomography scanner using x-ray radiation, scattered radiation occurs in a transverse direction to the x-ray radiation emanating from a focus of an x-ray source by interaction of the x-ray radiation with the object. The scattered radiation causes artifacts in the images calculated from the attenuation values. The attenuation values are generally determined on the basis of the radiation transmitted through the object and detected by a detector. Hence, the artifacts impair the quality; this is disadvantageous particularly in the case of images used for medical diagnostic purposes.

In order to at least reduce the scattered radiation, so-called scattered radiation collimators are arranged upstream of the detector in the direction of incidence of the radiation. In general, the scattered radiation collimators comprise a multiplicity of scattered radiation absorber elements, shortened to absorber elements, which are aligned substantially in parallel or are aligned toward the focus of the radiation source, i.e. they can be confocal. The elements absorb the scattered radiation, which was scattered through the object, and are in general produced by an arbitrary material or an arbitrary material composition which is suitable for absorbing the scattered radiation in the case of a given thickness of the scattered radiation collimator elements, at least to the extent that the scattered-radiation dependent artifacts can be avoided as far as possible.

In the case of medical imaging, the scattered radiation absorber elements should at least have such absorption capabilities that the diagnostic quality of the images is not overly impaired. In the present context, this means that scattered-radiation dependent artifacts can at least be suppressed to the extent that the diagnostic significance of, for example, a tomographic image reconstructed from the attenuation values or a tomographic illustration is not overly reduced.

By way of example and without any restrictions to the generality, metals such as tungsten with carrier materials comprising metallic—or, in general, radiation-absorbing—particles, etc. can be used for the materials or material compositions of the scattered radiation collimator elements.

Furthermore, the scattered radiation absorber elements should have particularly small thickness tolerances, because they are arranged upstream of the detector, and be particularly stable against mechanical effects so that shadow-related artifacts can be avoided as far as possible.

Producing scattered radiation collimator elements in the form of the customary collimator sheets which satisfy the abovementioned requirements is complex: on the one hand due to the required small acceptable thickness tolerances and the high planarity, and on the other hand due to the possibly required high mechanical stability. This holds in particular for comparatively large-area and long scattered radiation collimator elements which span a number of detector elements like a bridge.

According to at least one embodiment of the invention, provision is now made for the scattered radiation collimator element to comprise a plurality of absorber elements which are designed in a strip-like or filament-like fashion and which are arranged adjacent to one another with respect to their longitudinal direction to form an absorber surface. Sometimes this implies that the absorber elements are designed to be smaller or narrower than the overall scattered radiation collimator element. Such absorber elements can be produced with less production complexity and, connected to this, with smaller production costs whilst satisfying more stringent thickness tolerances.

In order to achieve a particularly high planarity, so that shadow artifacts as a result of deviation from the planarity can be avoided, it is possible, for example, to position the absorber elements on a surface (produced once) with a high planarity and to fix the absorber elements thus arranged in a planar fashion. In particular, this makes it possible to achieve a high planarity with small production complexity and comparatively low costs.

By way of example, and without any restrictions to the generality, it is possible to implement this fixation by clamping from the edge, by the provision of a matrix produced by a curable material, or the like.

In order to in particular increase the stability of the scattered radiation collimator element, a first group of absorber elements can be, with respect to their longitudinal direction, aligned in a first direction and a second group of absorber elements can be, with respect to their longitudinal direction, aligned in a second direction which runs obliquely with respect to the first direction. The first direction and the second direction can in this case be perpendicular to one another, or subtend an angle between 0 degrees and 90 degrees. In the case of the absorber elements having a substantially constant thickness or width in their longitudinal direction, this results in a substantially parallel arrangement of the absorber elements in the first and second directions. This eases the arrangement of the absorber elements.

The abovementioned arrangements can in particular be designed such that the first and second groups form a cross-like mesh. In this case, a stabilizing effect can achieved in an advantageous fashion by arranging the absorber elements to run above and below one another in a substantially crisscross fashion, i.e. by the cross-like mesh, and as a result of the meshing of the absorber elements of the first and second groups connected to this.

The stabilizing effect is advantageous in x-ray computed tomography devices, in particular. In general, x-ray computed tomography devices scan an examination object in a circular or helical fashion, the x-ray tube and the radiation detector unit rotating about a system axis. In general, the direction of the system axis is referred to as the z-direction, while the azimuthal direction with respect to the system axis is referred to as the phi-direction ($\phi$-direction).

In the phi- and z-directions, the abovementioned radiation detector units can in each case comprise a plurality of detector modules arranged next to each other. The achievable high mechanical stability can at least avoid a deformation of the scattered radiation collimator elements as a result of centrifugal forces and the like, and thus causing shadow artifacts.

A second aspect of at least one embodiment of the invention relates to a scattered radiation collimator comprising a plurality of scattered radiation collimator elements according to at least one embodiment of the invention. In this case, the scattered radiation collimator elements can be arranged such that their absorber surfaces are facing one another. Possible alignments include, for example, a parallel alignment or alignment toward a focus of a radiation source, i.e. a confocal alignment.

A third aspect of at least one embodiment of the invention relates to a radiation detector unit for detecting x-ray or gamma radiation. The radiation detector unit comprises one or more radiation detector modules and one or more scattered radiation collimators according to the invention arranged upstream of the radiation detector module(s) in the direction of incidence of the radiation. A substantially arbitrary number of scattered radiation collimators can be selected for every radiation detector module, in particular in accordance with the circumstances and the respective requirements regarding the degree of absorption and the shape of the radiation detector modules. In the case of a radiation detector unit with radiation detector modules arranged like tiles in two dimensions, the scattered radiation collimator(s) can have scattered radiation collimator elements arranged in two dimensions. In the example case of x-ray computed tomography, the scattered radiation collimator elements can thus be arranged in the z-direction and/or in the phi- direction.

Advantages and advantageous effects of the second and third aspect of embodiments of the invention emerge from the explanations regarding the first aspect of at least one embodiment of the invention.

A fourth aspect of at least one embodiment of the invention relates to a method for producing a scattered radiation collimator element according to at least one embodiment of the invention, at least comprising the following steps:

producing a multiplicity of absorber elements with a strip-like or filament-like design in order to absorb x-ray or gamma radiation, and arranging the absorber elements adjacently to one another with respect to their longitudinal direction in order to form the scattered radiation collimator element such that an absorber surface for absorbing scattered radiation is formed.

In accordance with refinements of the scattered radiation collimator element according to at least one embodiment of the invention, the method provides for the possibility of a first group of absorber elements to be aligned in a first direction and a second group of absorber elements to be aligned in a second direction which runs obliquely with respect to the first direction. Furthermore, the first and the second groups can be aligned such that the first direction is perpendicular to the second direction or that the first and second directions subtend an angle of between 0 degrees and 90 degrees. Moreover, the step of adjacent arrangement to one another can comprise interweaving to form a cross-like mesh. Finally, the absorber elements which are arranged adjacent to one another or interwoven can be mechanically stabilized by a curable material.

The method makes it possible to produce the scattered radiation collimator element according to at least one embodiment of the invention in a particularly simple and cost-effective manner due to its advantages and advantageous effects. At the same time, it is possible to produce a particularly stable scattered radiation collimator element having a high planarity and low thickness tolerances.

BRIEF DESCRIPTION OF THE DRAWINGS

In the following text, example embodiments of the invention and the advantages and advantageous effects thereof will be explained in more detail on the basis of the figures, in which

FIG. 3 schematically shows a flowchart of a method in accordance with the fourth aspect of an embodiment of the invention.

DETAILED DESCRIPTION OF THE EXAMPLE EMBODIMENTS

Figure 1:
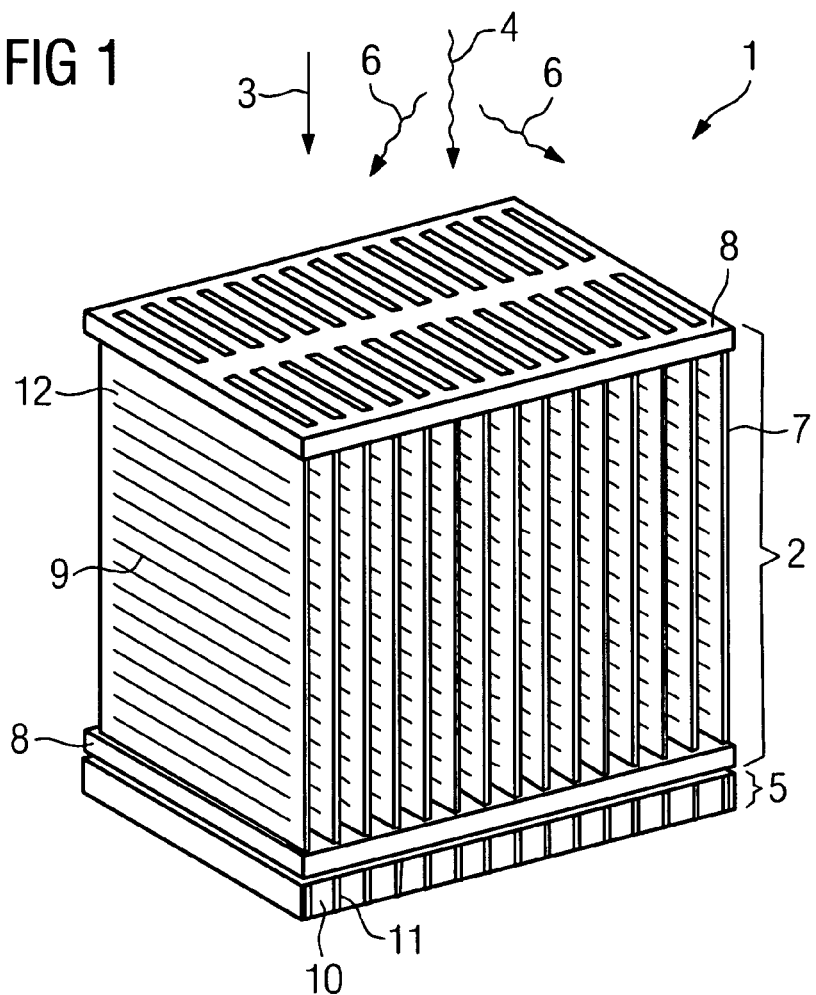
FIG. 1 shows a radiation detector unit in accordance with the third aspect of an embodiment of the invention having a scattered radiation collimator in accordance with the second aspect of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, identical or functionally identical elements are always provided with the same reference symbol. The illustrations in the figures are schematic and not necessarily true to scale, with it being possible for the scale to vary between the figures. In the following text, and without restricting the generality, the radiation detector unit and the scattered radiation collimator are only discussed to the extent considered necessary for understanding an embodiment of the invention.

FIG. 1 shows a radiation detector unit 1 in accordance with the third aspect of an embodiment of the invention having a scattered radiation collimator 2 in accordance with the second aspect of an embodiment of the invention. The scattered radiation collimator 2 is arranged upstream of a radiation detector module 5 in the direction of incidence 3 of the radiation 4 (e.g. x-ray or gamma radiation) which is to be detected by way of the radiation detector unit 1.

The radiation detector module 5 can be designed as an x-ray or gamma ray detector module. In the case of the present example embodiment, the radiation detector unit 1 only has one radiation detector module 5 and one scattered radiation collimator 2. However, within the scope of embodiments of the invention, it is also possible for the radiation detector unit 1 to have a plurality of radiation detector modules 5, arranged, in particular, like tiles in one or two dimensions. In this case, in accordance with FIG. 1, every radiation detector module 5 can respectively have arranged upstream of it a separate scattered radiation collimator 2. However, it is also possible for a scattered radiation collimator 2 to span several radiation detector modules 5, or for a number of adjacent scattered radiation collimators 2 to be arranged upstream of one radiation detector module 5. On this note, the number of scattered radiation collimators 2 per radiation detector module 5 is not important, and the statements regarding the refinement shown in FIG. 1 apply in analogous fashion to other refinements lying within the scope of embodiments of the invention.

The radiation detector unit 1 shown in FIG. 1 can be used to examine an object (not shown) using the radiation 4. In the process, the object is scanned by the radiation 4, i.e. the radiation 4 is directed onto the object and passes through it. As it passes through the object, the radiation 4 is attenuated in accordance with the, in particular local, absorption properties of the object. By detecting the radiation transmitted through the object in the form of attenuation values, for example, information regarding the inner structure of the object can be obtained. In the case of x-ray computed tomography, the object is scanned in an e.g. circular or helical fashion, and the attenuation values obtained can be used to calculate a two- or three-dimensional slice image of the object.

As the radiation 4 passes through the object, it is not only attenuated, but scattered radiation 6 is also generated by interaction of the radiation 4 with the object. The scattered radiation 6 falsifies the attenuation values and impairs, for example, the quality of the images or displays determined from the attenuation values.

The scattered radiation collimator 2 is used to absorb the scattered radiation 6 at least such that the quality is not overly impaired and sufficiently reliable statements about the inner structure of the object can be obtained. In the case of medical imaging, e.g. by way of x-ray computed tomography, the scattered radiation 6 should at least be absorbed such that the diagnostic quality of the images is not significantly impaired by the scattered radiation 6 so that sufficiently reliable diagnosis can be ensured.

The scattered radiation collimator 2 in accordance with FIG. 1 has a multiplicity of scattered radiation absorber elements 7 to absorb the scattered radiation 6, at least to the extent described above. The scattered radiation absorber elements 7 are held by means of a support 8 which, together with the scattered radiation absorber elements 7, is attached on the inbound-radiation side of the radiation detector module 5.

In the example shown in FIG. 1, the scattered radiation absorber elements 7 are arranged such that absorber surfaces 9 of adjacent scattered radiation absorber elements 7 face one another. The scattered radiation absorber elements 7 can be aligned substantially parallel with respect to one another, or toward a focus of radiation source (not shown) i.e. in a confocal fashion.

The scattered radiation collimator 2 limits the maximum possible angle of incidence of the radiation 4 on the radiation detector module 5. This makes it possible to effectively absorb the scattered radiation 6 which in general has a relatively large angle of incidence. Since the scattered radiation absorber elements 7 have a finite thickness, and hence a non-negligible absorption cross-section in the direction of incidence of the radiation, part of the radiation 4 which is incident on the scattered radiation absorber elements in a substantially perpendicular fashion is also absorbed. This leads to a shadow on the radiation detector module 5.

Since the radiation detector module 5 has a multiplicity of detector elements 10, depending on the desired spatial resolution, and because shadows should be avoided, e.g. to increase the detection accuracy, the scattered radiation absorber elements 7 are arranged such that they lie above inactive zones 11 of the radiation detector module 5, that is to say above inactive zones 11 between adjacent detector elements 10. In the case of conventional tomography equipment, these inactive zones 11 have, for example, a width in the region of 100 μm. Accordingly, it is necessary for the scattered radiation collimator elements 7 to have a thickness (which includes possible production-related thickness tolerances) which does not exceed the predetermined width.

Exceeding the predetermined width would lead to shadows which in turn lead to artifacts in the images calculated from the attenuation values. Likewise, shadows which are caused by deformation of the scattered radiation collimator elements 7 as a result of external influences, such as acceleration forces, oscillations and the like, should be avoided. This shows that delicate scattered radiation collimator elements 7 are required which have a thickness of the order of 100 μm or even less, particularly small thickness tolerances and high planarity and moreover are particularly stable. The production of such scattered radiation collimator elements 7 as conventional thin sheet-strips, so-called collimator sheets, is complex and expensive if it can even be implemented technically.

It is for these reasons that the scattered radiation collimator element 7 according to the invention comprises a number of strip-like or filament-like absorber elements 12 which, in accordance with the abovementioned requirements, can be produced in a simpler and more cost-effective manner. In FIG. 1, the absorber elements 12 are arranged adjacent to one another, parallel to their longitudinal direction, which, for simplicity, is only shown for two scattered radiation collimator elements 7 located on the left-hand side.

Figure 2:
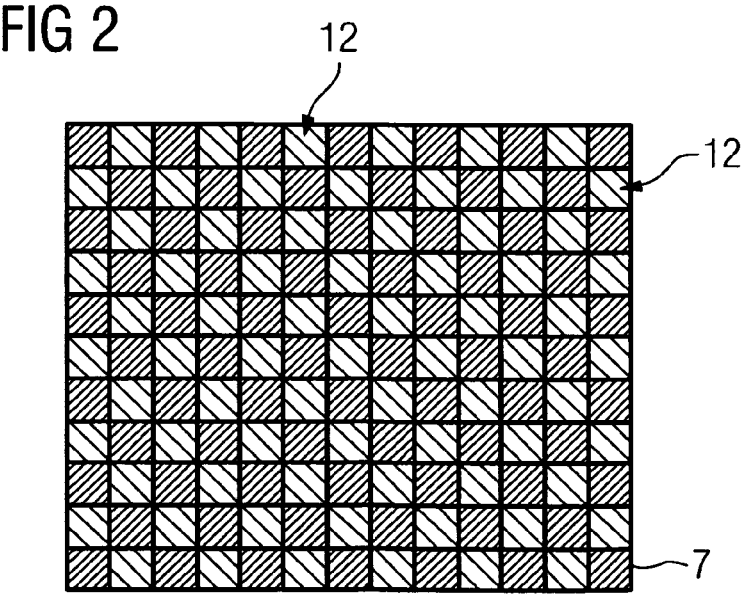
FIG. 2 shows a detailed view of a scattered radiation collimator element in accordance with the first aspect of an embodiment of the invention.

In contrast to FIG. 1, the absorber elements 12 in the detailed view of FIG. 2 are arranged in a woven fashion, overlapping in a cross-like fashion. The woven structure makes it possible to have an additional stability advantage. Any other structures for arranging the absorber elements 12 are feasible, e.g.: overlapping, double layered, particularly cross-like double layered, etc.

In order to ensure the required stability of the scattered radiation collimator elements 7, they can be clamped into the support 8, for example. The stability can also be improved by strengthening the absorber elements 12 using a curable material such as a resin. In this case, the support 8 can comprise the matrix.

In the present example embodiment, the scattered radiation collimator elements 7 are arranged parallel to one direction only. Depending on the design of the radiation detector module 5 and the desired scattered radiation absorption, it is also possible for the scattered radiation collimator elements 7 to be arranged in two directions running obliquely with respect to one another. The latter arrangement is particularly suited to radiation detector modules 5 which have a two-dimensional pixelation, i.e. which have detector elements 10 arranged in the form of a matrix.

FIG. 3 schematically shows the process of producing a scattered radiation collimator element 7. Firstly, a multiplicity of absorber elements 12 are produced. Since the absorber elements 12 are comparatively small or narrow compared to the overall size of a scattered radiation collimator element 7, they can be produced in a simpler and more cost-effective manner given the respective requirements. In a further step, the absorber elements 12 are arranged adjacent to one another in parallel with their longitudinal direction and are connected to form a scattered radiation collimator element 7, for example by means of a curable synthetic resin. In this case, the absorber elements 12 can be positioned and aligned on a once produced, highly planar surface, as a result of which the required planarity can be ensured.

Only three absorber elements 12 are shown within the scope of FIG. 3 for the sake of simplicity. It is understood that the number of absorber elements 12 depends on, inter alia, the size of the desired scattered radiation collimator element 7 and the width or thickness of the absorber elements 12. In this respect, the selected number only serves for illustrative purposes and should not be seen as limiting. In accordance with embodiments of the invention, the absorber elements 12 can also be positioned differently with respect to one another, e.g. overlaying or interwoven in a cross-like fashion, etc.

The description above in particular makes it clear that the scattered radiation collimator element according to an embodiment of the invention, the scattered radiation collimator, the radiation detector unit and the method are suited to achieving the object on which an embodiment of the invention is based. That is to say, provision can be made for, in particular, a highly planar scattered radiation collimator element which can be produced in a particularly simple and cost-effective manner and which at the same time has a high mechanical stability.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A scattered radiation collimator element for a scattered radiation collimator configured to absorb scattered radiation generated during an examination of an object by interaction of x-ray or gamma radiation used for this purpose with the object, the scattered radiation collimator element comprising:
a plurality of absorber elements, each of the absorber elements being a strip or filament segment, and being arranged adjacent to one another with respect to their longitudinal direction to form a planar absorber surface of the scattered radiation collimator element.

2. The scattered radiation collimator element as claimed in claim 1, wherein a first group of the plurality of absorber elements is, with respect to their longitudinal direction, aligned in a first direction and a second group of the plurality of absorber elements is, with respect to their longitudinal direction, aligned in a second direction which runs obliquely with respect to the first direction.

3. The scattered radiation collimator element as claimed in claim 2, wherein the absorber elements of the first group and the second group are interwoven to form a cross-like mesh.

4. The scattered radiation collimator element as claimed in claim 2, wherein the plurality of absorber elements are mechanically stabilized by a matrix produced by a curable material.

5. A scattered radiation collimator comprising:
a plurality of scattered radiation collimator elements as claimed in claim 2, wherein absorber surfaces of the plurality of scattered radiation collimator elements face one another.

6. A radiation detector unit for detecting x-ray or gamma radiation, comprising:
one or more radiation detector modules; and
one or more scattered radiation collimators as claimed in claim 5, arranged upstream of the one or more radiation detector modules in the direction of incidence of the x-ray or gamma radiation.

7. The scattered radiation collimator element as claimed in claim 1, wherein a first group of the plurality of absorber elements is, with respect to their longitudinal direction, aligned in a first direction and a second group of the plurality of absorber elements is, with respect to their longitudinal direction, aligned in a second direction, and wherein the first and second directions subtend an angle of less than or equal to 90 degrees.

8. The scattered radiation collimator element as claimed in claim 7, wherein the absorber elements of the first group and the second group are interwoven to form a cross-like mesh.

9. The scattered radiation collimator element as claimed in claim 1, wherein the plurality of absorber elements are mechanically stabilized by a matrix produced by a curable material.

10. A scattered radiation collimator comprising:
a plurality of scattered radiation collimator elements as claimed in claim 1, wherein absorber surfaces of the plurality of scattered radiation collimator elements face one another.

11. A radiation detector unit for detecting x-ray or gamma radiation, comprising:
one or more radiation detector modules; and
one or more scattered radiation collimators as claimed in claim 10, arranged upstream of the one or more radiation detector modules in the direction of incidence of the x-ray or gamma radiation.

12. The scattered radiation collimator element of claim 1, wherein the plurality of absorber elements are arranged adjacent to one another in a direction of incident radiation.

13. The scattered radiation collimator element of claim 1, wherein the scattered radiation collimator element is configured as a single component of a scattered radiation collimator including a plurality of collimator elements, the single component having only two absorber surfaces.

14. A method for producing a scattered radiation collimator element for a scattered radiation collimator, the method comprising:
producing a plurality of absorber elements, each of the plurality of absorber elements being a strip or filament segment, and designed to absorb x-ray or gamma radiation; and
arranging the plurality of absorber elements adjacent to one another with respect to their longitudinal direction to form a planar absorber surface of the scattered radiation collimator element, the absorber surface being for absorbing scattered radiation.

15. The method as claimed in claim 14, wherein a first group of the plurality of absorber elements is aligned in a first direction and a second group of the plurality of absorber elements is aligned in a second direction which runs obliquely with respect to the first direction.

16. The method as claimed in claim 15, wherein the arranging comprises interweaving to form a cross-like mesh.

17. The method as claimed in claim 16, wherein the plurality of absorber elements which are arranged adjacent to one another are mechanically stabilized by a curable material.

18. The method as claimed in claim 15, wherein the plurality of absorber elements which are arranged adjacent to one another are mechanically stabilized by a curable material.

19. The method as claimed in claim 14, wherein a first group of the plurality of absorber elements is aligned in a first direction and a second group of the plurality of absorber elements is aligned in a second direction, and wherein the first and second groups are aligned such that the first direction and second direction subtend an angle of less than or equal to 90 degrees.

20. The method as claimed in claim 19, wherein the arranging comprises interweaving to form a cross-like mesh.

21. The method as claimed in claim 19, wherein the plurality of absorber elements which are arranged adjacent to one another are mechanically stabilized by a curable material.

22. The method as claimed in claim 14, wherein the plurality of absorber elements which are arranged adjacent to one another are mechanically stabilized by a curable material.

* * * * *